US011638720B1

(12) United States Patent
Brady et al.

(10) Patent No.: US 11,638,720 B1
(45) Date of Patent: May 2, 2023

(54) RISK MITIGATION OF INFECTIOUS DISEASE TRANSMISSION FROM INCIDENTAL AND INTIMATE CONTACT USING ATOMIC SCALE MOLECULAR DISRUPTION AND BIOCIDAL HALO-FULLERENES DELIVERED VIA TOPICAL, FLUSHING AND ENTERAL MECHANISMS

(71) Applicants: Terry Earl Brady, The Valley (AI); Anthony Lee Dellinger, Burlington, NC (US); Lowell Hughes, The Valley (AI); Melinda K. M. Goddard, The Valley (AI); Julie Catherine-Elise Hakim, Houston, TX (US)

(72) Inventors: Terry Earl Brady, The Valley (AI); Anthony Lee Dellinger, Burlington, NC (US); Lowell Hughes, The Valley (AI); Melinda K. M. Goddard, The Valley (AI); Julie Catherine-Elise Hakim, Houston, TX (US)

( * ) Notice: Subject to any disclaimer, the term of this patent is extended or adjusted under 35 U.S.C. 154(b) by 0 days.

(21) Appl. No.: 17/973,753

(22) Filed: Oct. 26, 2022

Related U.S. Application Data

(60) Provisional application No. 63/397,950, filed on Aug. 15, 2022.

(51) Int. Cl.
| | | |
|---|---|---|
| *A61K 33/18* | (2006.01) | |
| *A61K 9/00* | (2006.01) | |
| *A61K 31/19* | (2006.01) | |
| *A61K 33/00* | (2006.01) | |
| *A61K 33/16* | (2006.01) | |
| *A61K 33/20* | (2006.01) | |
| *A61K 36/00* | (2006.01) | |
| *A61K 36/14* | (2006.01) | |
| *A61K 36/23* | (2006.01) | |
| *A61K 36/28* | (2006.01) | |
| *A61K 36/288* | (2006.01) | |

(Continued)

(52) U.S. Cl.
CPC ............ *A61K 33/18* (2013.01); *A61K 9/0095* (2013.01); *A61K 31/19* (2013.01); *A61K 33/00* (2013.01); *A61K 33/14* (2013.01); *A61K 33/16* (2013.01); *A61K 33/20* (2013.01); *A61K 36/00* (2013.01); *A61K 36/14* (2013.01); *A61K 36/23* (2013.01); *A61K 36/28* (2013.01); *A61K 36/288* (2013.01); *A61K 36/30* (2013.01); *A61K 36/45* (2013.01); *A61K 36/734* (2013.01); *A61K 36/75* (2013.01)

(58) Field of Classification Search
CPC ........ A61K 33/18; A61K 31/19; A61K 33/00; A61K 33/14; A61K 33/16; A61K 33/20; A61K 36/00; A61K 36/14; A61K 36/23; A61K 36/28; A61K 36/288; A61K 36/30; A61K 36/45; A61K 36/734; A61K 36/07; A61K 9/0095
See application file for complete search history.

(56) References Cited

U.S. PATENT DOCUMENTS

| 6,696,077 B2 * | 2/2004 | Scherr ..................... A61L 15/28 |
| | | 424/443 |
| 2013/0041185 A1 * | 2/2013 | Kokubo .................. C07C 29/62 |
| | | 568/808 |

OTHER PUBLICATIONS

Campos, M.D., Zucchi, P.C., Phung, A., Leonard, S.N. and Hirsch, E.B. The activity of antimicrobial surfaces aries by testing protocol utilized PLoS One, 2016, p. e0160728, vol. 11, No. 8.

(Continued)

*Primary Examiner* — Michael P Cohen

(57) ABSTRACT

The present invention pertains to quantum-scale biocidal particles and chemical reactions that disrupt and eviscerate microbial matter by combining aqueous and dry components. As halo-fullerene activation requires volatile excitation to mix, contact and collide so as to rupture microbial matter, atomic scale chemical reactions impart the requisite movement of engineered halo-fullerenes to destroy bacterial, fungal and viral matter upon contact.

The present invention includes two primary mechanisms: an excitation chemistry and biocidal, hydrophobic halo-fullerenes. Upon aqueous exposure, the dry composition initiates a chemical reaction that activates biocidal halo-fullerenes to disrupt biologic surfaces in topical applications. The object of the present invention is a shelf stable, pre-packaged wiping material or dry packet for rehydration with broad spectrum antimicrobial activity. In one example, a matrix or wipe material would be comprised of densely packed and highly concentrated halo-fullerenes and a chemical reaction stimulant. When activated upon aqueous exposure, it would relax water molecules, alter hydrogen binding, and disrupt adhesion and cohesion forces that characterize surface tensions. These dynamics would then isolate sebaceous substances and free oxygen radicals, along with outgassing of carbon dioxide. The chemical reaction stimulant thus transfers energy and hyperactivates otherwise inert halo-fullerenes to form a biocidal composition.

Broader utilities range from topical cleansing for personal hygiene, as well as various clinical and surgical procedures, as surgical and prophylactic lavage and rinse solutions, and enteral formulations as a hypertonic renal flush combined with short-acting diuresis. The halo-fullerene and hypertonic renal flush would cause osmotic cellular outflow, mitigate cellular microbial uptake and initial seroconversion and bloodborne events, while a botanical diuretic agent would facilitate systemic prophylaxis or treatment of UTIs.

19 Claims, No Drawings

(51) Int. Cl.
    *A61K 36/30* (2006.01)
    *A61K 36/45* (2006.01)
    *A61K 36/734* (2006.01)
    *A61K 36/75* (2006.01)
    *A61K 33/14* (2006.01)

(56) References Cited

OTHER PUBLICATIONS

Center for Disease Conrol and Prevention. Reported STDs Reach All-time High for 6th Consecutive fear. CDC Newsroom Press Releases. Apr. 13, 2021. Link retrieved from: https://www.cdc.gov/media/releases/2021/p0413-stds.html.

Center for Disease Conrol and Prevention. COVID-19 Impact on HAIs in 2021. CDC Hospital Associated Infections Data Portal. Jun. 10, 2022 Link retrieved from: https://www cdc.gov/hai/data/portal/covid-impact-hai.html.

Center for Disease Conrol and Prevention. Safer Sex, Social Gatherings, and Monkeypox. Sep. 9, 2022. Link retrieved from: https://www.cdc.gov/poxvirus/monkeypox/prevention/sexual-health.html.

Collins, A.S. Preventing Health Care-Associated Infections. Hughes RG, editor. Patient Safety and Quality: An Evidence-Based Handbook for Nurses. Apr. 2008. Chapter 41. Rockville (MD): Agency for Healthcare Research and Quality (US).

Chugh, T. Diagnostic errors in clinical microbiology and antimicrobial resistance. Current Medicine Research and Practice, 2020, pp. 27-29, vol. 10, No. 1.

Dargère, S., Cormier, H. and Verdon, R. Contaminants in blood cultures: importance, implications, interpretation and prevention. Clinical Microbiology and Infection, 2018, pp. 964-969, vol. 24, No. 9.

Feldman, C. and Anderson, R. The role of co-infections and secondary infections in patients with COVID-19. Pneumonia, 2021, pp. 1-15, vol. 13, No. 1.

O'Neill, J. Antimicrobial resistance: tackling a crisis for the health and wealth of nations. Review on Antimicrobial Resistance. Dec. 2014.

Rhee, C., Jones, T.M., Hamad, Y., Pande, A., Varon, J., O'Brien, C., Anderson, D.J., Warren, D.K., Dantes, R.B., Epstein, L. and Klompas, M. Prevalence, underlying causes, and preventability of sepsis-associated mortality in US acute care hospitals. JAMA Network Open, 2019, pp. e187571-e187571, vol. 2, No. 2.

Seifi, B., Sahbaei, F., Zare, M.Z., Abdoli, A. and Heidari, M. A Comparative Study Between Povidone-iodine and Manugel 85 on Surgical Scrub. Materia socio-medica, 2016, p. 348, Vo.. 28, No. 5.

World Health Organization. Sexually transmitted infections (STIs). WHO Newsroom Fact sheets. Aug. 22, 2022. Link retrieved from: https://www.who.int/news-room/fact-sheets/detail/sexually-transmitted-infections-(stis).

Zeng, Z., Zhan, J., Zhang, K., Chen, H. and Cheng, S. Global, regional, and national burden of urinary tract infections from 1990 to 2019: an analysis of the global burden of disease study 2019. World Journal of Urology, 2022, pp. 755-763, vol. 40, No. 3.

\* cited by examiner

RISK MITIGATION OF INFECTIOUS DISEASE TRANSMISSION FROM INCIDENTAL AND INTIMATE CONTACT USING ATOMIC SCALE MOLECULAR DISRUPTION AND BIOCIDAL HALO-FULLERENES DELIVERED VIA TOPICAL, FLUSHING AND ENTERAL MECHANISMS

CROSS REFERENCE TO RELATED APPLICATION(S)

This application claims priority to U.S. Provisional Patent Application Ser. No. 63/397,950 filed on Aug. 8, 2022.

FIELD OF THE INVENTION

The present invention relates to an antimicrobial composition with demonstrable sterilizing or decontaminating capabilities, and more specifically to antimicrobial mixtures containing halogen functionalized fullerenes and volatile chemistries that kinetically disrupt environmental pathogens to disinfect skin, mucosa and internal physiologic regions. Intended uses include personal protection and hygiene, infection risk mitigation, as well as venipuncture, injection and surgical site preparation, cleansing rinses and irrigation, systemic diuresis, as well as non-biological or other surfaces for disinfecting purposes.

BACKGROUND OF THE INVENTION

Epidemiologically, infectious diseases have entered an era of remark, particularly with respect to dermal contact transmission. The international flow of people and goods eludes most preventive measures, as micron-sized microbes continually cross borders, permeate and can thrive in nearly all conditions and spaces, as well as both in and on unsuspecting travelers. Complex modes of disease transmission from both intimate and incidental contact associated with Monkeypox was also recently reported by the CDC (CDC, 2022b). Critical risk factors include pathogen load, infection pathway and microbial dwell time. That is, the presence, number and virulence of microbial matter are ultimately the determinants of whether the site becomes infected. These risks are thus ubiquitous, and transmission, resistance and lethality of contagious agents are increasing. Underlying the broader incidence of infectious disease are sepsis statistics, whereby many such cases are caused by hapless hygiene habits combined with often benign abrasions, allowing entry of pathogens into the bloodstream. In turn, sepsis is already the leading cause of untimely deaths and is projected to become the leading cause of global mortality during the next generation (Rhee et al., 2019; O'Neill, 2014). As globalization continues, innovations that mitigate infectious disease transmission risks through timely microbial disruption, reduced pathogen concentration and clearance of pathways are thus vital, as illustrated by historical and contemporary endemics and pandemics.

While the need for better means and methods of infectious disease prevention exploded into public awareness during the SarsCOV-2 pandemic, urinary tract infections (UTIs), sexually transmitted diseases (STDs) including human papilloma virus (HPV), and hospital acquired infections (HAIs) have posed longstanding public health challenges for decades before the most recent pandemic began. UTIs have increased from 250 to 404.6 million between 1990 and 2019, an increase of approximately 152.4 million cases (Zeng et al., 2022). In 2021, the CDC reported that STDs have reached a new high for a sixth consecutive year (CDC, 2021); whereas, the World Health Organization has estimated that more than 1 million STDs are acquired every day worldwide, the majority of which are asymptomatic (WHO, 2022). Despite advanced surveillance and personal protective hygiene methods employed during the pandemic, the CDC reported as much as a 47% increase in the incidence of HAI (CDC, 2022a). These data are consistent with trends in antimicrobial resistance (AMR) and highlight the shortcomings and need for more effective institutional and individual preventive approaches.

HAIs also remain an overarching problem directly linked to pathogen virulence, AMR, and rapidly evolving microbes. Their paradoxical persistence remains challenging in some of the most pristine settings in healthcare. That said, pre-surgical hand and arm washing with halogen-enriched soaps (i.e., povidone-iodine) alters the characteristics of skin, and surgical "scrubbing in" with respect to both technique and duration, are proven methods for HAI mitigation. As such, when standardized hospital hygiene practices are followed, the incidence of HAI is reduced (Collins, 2008).

UTIs, HPV and numerous bacterial, fungal and other viral infections are often sexually transmitted due to pathways conducive to microbial growth, compounded by pathogen load and exposure duration. UTI and STD prevention can thus often be achieved through pre- and post-coital hygiene methods.

Nonetheless, measurement of overall infection rates and diagnostic medicine are often confounded by cross-contamination or insufficient sampling in various fluid and tissue specimens. With respect to sepsis, among the most dangerous of infectious diseases, cross-contamination in blood cultures, the "gold standard" of detection, has been estimated at 50% (Dargère et al., 2018). In particular, the diagnostic shortcomings of blood culture have driven the unsustainable practice of empiric antibiotic therapy beyond stewardship guidelines and contributed to AMR of various pathogens (Chugh, 2020). Most blood culture cross-contamination occurs during venipuncture, notwithstanding needle-stick sites being typically cleansed by experienced phlebotomists. Despite meticulous standards, the diagnostic unreliability of blood culture persists largely due to the endemic, complex dermal attachment of microbes encompassing layered surfaces in various stages of cellular development, moisture levels, cell size and separation, and pathogen movement and burrowing. In turn, skin infections can include particularly pathogenic diseases such as Methicillin-resistant *Staphylococcus aureus* (MRSA), adding untenable risks to otherwise routine phlebotomy. Thus, effective skin decontamination for both injections and venipuncture—as well as sexually transmitted UTIs and other infections, can require overcoming a sort of microbial skin symbiosis by employing more volatile surface reactions to dislodge pathogens and facilitate contact with biocides. The ability to cleanse the area before and after any procedure with an antimicrobial towelette can thus play a crucial role in healthcare infection prevention.

In general, as contamination pertains to human anatomy, blood, tissue, and cell cultures remain the state of the art despite reliability issues. In fact, the term "sterile" does not necessarily apply to a specific assay or guidelines for measuring microbes on surfaces, such as the skin, oral cavity, urethra, or vagina. This is notwithstanding fluids and tissues considered to be sterile, including: cerebrospinal, vitreous, synovial, pleural, peritoneal, and pericardial fluids; blood, urine, bone marrow, and lymph nodes; as well as the brain, heart, liver, spleen, kidneys, pancreas, ovaries, testes, muscle and vascular tissues. Sterility assays established under ISO and ASTM standards, per se, have been adopted for non-biological applications, e.g., surgical instruments, injection fluids and drugs, defined fields (i.e., surgical suite), plastic or glassware, syringes, specialized coatings, and other materials, whereby the presence of microbes may be deleterious (Campos et al., 2016). In this context, sterile refers to the absence of microorganisms, but it does not exclude pyrogens or endotoxins, which are non-proliferating, non-infectious inflammatory agents. Although antimicrobial activity measurements on material surfaces employ defined equations associated with changes in viable microorganism counts in defined spaces over specific periods, such methods and metrics have not been developed for assessing biologic surfaces like the skin.

In turn, zoonosis and subsequent mutation have contributed to further pathogen diversity and confounding of preventive measures, epidemiologic monitoring and vaccine development. While zoonosis has been widely accepted as the vector causing the SarsCOV-2 pandemic, suboptimal vaccination rates have compounded its impact through further mutations. Contrarian vaccination social trends, especially as recently observed, have further challenged medical science, diminished institutional credibility and undermined decades of immunology research and vaccine progress. While protective and preventive hygiene issues were roiling at the height of the SarsCOV-2 pandemic, co-infections from secondary pathogens, many known to be antibiotic resistant, nonetheless accounted for a disproportionate share of mortal outcomes, complicated further by indiscriminate use of such drugs (Feldman and Anderson, 2021). Another example of a preventable public health outcome is the incidence of cervical cancer; whereby higher rates of adolescent HPV vaccinations could significantly reduce such cases, given the established correlation and frequency of such sequelae from sexually transmitted HPV. Clearly, both individual and institutional efforts to prevent transmission are required to mitigate risks and ultimately prevent infectious disease.

As such, individual interventions can enhance infection risk management and prevention, as evidenced by vaccination decisions and compliance with preventive hygiene guidelines. While disruptive eradication of fragile microbes appears simple, the data suggest otherwise. While the architecture of the dermis and epidermis act as a protective barrier, skin is not inherently antimicrobial. The temperature as well as the sebaceous and aqueous characteristics of skin create an environment for microbial compatibility. Despite time-tested methods intended to wash away or eviscerate dermal pathogens, it remains difficult to accomplish. Such evidence is informed by pre-surgical hand washing techniques, whereby scrubbing with dilute iodine soap often falls short of eliminating HAI transmission risks. These are reflected not only in surgical scrubbing data, but also in the increasing incidence of incision site infections emanating from antimicrobial-resistant pathogens.

With respect to STDs, alleviating UTI and STD infections also requires individual awareness strategies and practicable innovations for prevention. Established practices include the need for hydration and post-coital urine flushing, as well as the use of specialized vaginal douches and cleansing wipes.

Given risks of exposure to transmissible (airborne) pathogens during air travel, social gatherings, or as a prophylactic measure for front-line workers in hazardous environments (e.g., hospital and ambulatory healthcare staff), various methods have proven useful in cleansing nasal and nasopharyngeal cavities. These typically involve an isotonic saline solution under pressure that flows into one nostril, passes through the sinuses, and exits the opposite nostril. Other techniques include "neti" methods using steam for rinsing nasal passages without direct pressure; however, specific biocidal components may prove more beneficial in such applications.

Improvements in the formulation and chemistry associated with cleansing tissues and solutions have nonetheless been limited. The use of harsher chemistries, at higher concentrations may improve cleansing but can also damage dermal and mucosal cells and tissues. Nonetheless, formulations at lower concentrations can render the chemistry less biocidal and lead to a loss of efficacy. The current technical gaps in both prophylactic hygiene and diagnostics would thus benefit from innovation that dislodges and eviscerates pathogens while remaining harmless to cells under normothermic or cold sterilization.

BRIEF SUMMARY OF THE INVENTION

The purpose of this invention is a physiological sterilizing composition formulated using nontoxic, domiciliary agents in stable formats until wetted or mixed with an aqueous solution. This invention is a biocidal composition of halo-fullerenes that decontaminate a site or cavity—and as a therapeutic diuretic when used systemically. The material is benign and non-toxic to human cells and tissues. The halo-fullerenes impart antibacterial, antifungal and antiviral synergies for broad efficacy. Secondarily, the composition includes a chemical reaction stimulant that is activated through aqueous exposure. This reaction is characterized by lyophilized sodium bicarbonate, acetic acid and a sudsing or foaming agent.

The reactant chemistries of the composition reduce surface tensions; displace air, dirt, debris and microbial matter; and emulsify oils. Exposing the composition to an aqueous agent activates the lyophilized chemical reaction between the sodium bicarbonate and acetic acid. The first reaction is an acid-base interaction, whereby the hydrogen ions react with the sodium and bicarbonate ions to create carbonic acid and sodium acetate. Then a decomposition reaction follows, breaking down carbonic acid to water and carbon dioxide. In the presence of the foaming agent, gas sudsation bubbles are produced by the generation of carbon dioxide. The chemical reaction stimulant also actuates halo-fullerenes as broad-spectrum biocidal agents for robust halo-fullerene contact with complex skin architecture and dislodges entangled microbial matter. The combination of energized halo-fullerenes and surfactants interfere, interact, and damage the microbial membranes causing pathogen rupture and biocide. Applying the activated composition to a biological surface thus provides an immediate evisceration of microorganisms for an antiseptic effect.

Two preferred embodiments would include but not be limited to, a wipe, towelette or sponge material coated with dry reactant chemistries and halo-fullerenes—and a prepared vessel or package containing the dry ingredients with an optionally pre-measured diluent. The sealed, pre-packed, flexible and abrasive wiping material in the former embodiment (e.g., towelette, sponge, etc.) would be embedded with halo-fullerenes and a reaction stimulant chemistry that cause atomic scale kinetic energy from the reactions upon aqueous exposure. The reaction would mobilize halo-fullerenes and allow for comprehensive skin or tissue contact and evisceration of pathogens. In the latter embodiment, an array of decontaminating solutions could be employed for surgical cavity lavage, mouth and nasal rinses, and both douche and enema formulations. Decontamination would thus be achieved through exposing the composition to an aqueous solution and wiping, scrubbing or rinsing/irrigating the region.

Embodiments such as a surface wipe or towelette may have particular utility for pre- and post-coital personal hygiene used in the risk mitigation and/or prevention of UTIs and STDs. This application could also mitigate or prevent infections of non-reproductive organs, such as those transmitted by dermal and mucosal contact. The activated material in such embodiments could likewise be used as a sterilizing wipe before and after venipuncture/injection and surgical procedures.

Another embodiment would comprise a packaged dry enteral formulation to be mixed with a volume of water as directed for the prophylaxis or treatment of UTIs. Formulated as a hypertonic drink composition boosted by a botanical diuresis agent and hydrophobic halo-fullerenes in trace concentrations, upon ingestion, the hypertonic cellular status and expulsion fluid pathway would temporarily alter and prevent cellular uptake of microbial material. Subsequently, halo-fullerenes would bind and eviscerate microbial matter inside the kidneys, ureter, bladder and urethra, through which they would ultimately be excreted. The composition would alter osmosis dynamics to stimulate cellular outflow and urine production. Depending on the individual's metabolism, osmotic homeostasis would typically be reestablished within an hour or so, notwithstanding the need to void.

DETAILED DESCRIPTION OF THE INVENTION

The invention employs halogen particles covalently attached to fullerenes using standard chemical reactions as a primary biocidal agent in mitigation of risk and/or prevention of infectious diseases contracted through incidental or intimate contact. Halo-fullerenes are nanoscale particles that correspond in size to microbes, enabling rapid pathogen destruction without harming normal human cells, which are significantly larger than halo-fullerenes. In the invention, halo-fullerenes and microbial contact or collisions are further facilitated by kinetic energy created by the reaction stimulant. The volatile chemical reaction produces little heat, is extremely ephemeral, and likewise harmless to human cells and tissue.

The current invention also overcomes dermal and microbial compatibility as a function of tissue architecture associated with dermal porosity, temperature, and surface (e.g., scaly, flaky, rough) variables. Skin cells dwarf pathogens, and microbial propulsion and propagation energy enable colonization throughout the body. Functioning at atomic scale, once virtually weightless energy-intensive microbes infest and settle upon a physiologic surface, dislodging or eviscerating them is difficult. The present invention utilizes atomic scale reactions that create disruptive and chaotic forces to cleave molecular bonds and reduce surface tensions and aqueous barriers to leverage the antimicrobial chemistries of the composition. Stripping microbes from favorable aqueous or sebaceous envelopes would thereby release the microorganisms from protection, dislodging pathogenic matter with tumultuous carbon dioxide bubbling and hydrogen-bond cleavage that eviscerates the microbes, ruptured by accelerated halo-fullerene contact driven by the primary stimulant reaction.

In topical embodiments, the interface between the scrubbing material and the skin is characterized by a chemically reactive aqueous phase. Within this phase, a volatile reaction actuates halo-fullerenes, forming a destructive and biocidal environment that eradicates surface pathogens. The cohesive and adhesive properties of the aqueous interface are modified by the chemical reactions to allow for optimal contact and penetration throughout the application site. The result is complete, rapid microbial eradication and decontamination without vigorous scrubbing.

The composition is controllable, affordable and innocuous, using domiciliary chemistries that perturb and destroy tissue-microbial coexistence and mitigate infectious disease transfer. Particularly, the present invention describes a composition that disrupts and eradicates microbes through molecular scale contact and interactions without relying on caustic concentrations or harmful chemistries. The proposed invention does not create a pyrogen-free environment but pertains to topical scrubbing chemistry that produces a decontaminated field. Herein, the term sterile is used to define a biological specimen that has been rendered free of harmful microorganisms, and in some cases natural flora, but is not pyrogen-free. This invention does not apply to lung uptake of a pathogen except wherein the oral and nasal cavities may be cleansed of microbes before further migration into the lungs.

The present invention provides for a flexible and scrubbing material (e.g., towelette, sponge, wipe, etc.) as well as pre-packaged ingredients for rinse solutions upon mixing with water for cleansing a specified surface or cavity. The halo-fullerenes remain inert, absent the chemical reactions induced by aqueous activation of the invention. Exposing the dry reactant chemistries to an aqueous agent initiates reactions between the sodium bicarbonate, acetic acid and sudsing agent. This activation transfers energy to the halo-fullerenes in the material, which are then mobilized via the reaction stimulant. When applied to the skin—or flushed into bodily or surgical cavities, the reactant chemistries and antimicrobial halo-fullerenes are transferred to the skin or other tissues where they eradicate microbial matter.

The immediate effect is the reduction in microbes on or in the region after application. The efficacy of the composition of the present invention on a biological surface may be assessed using samples of the aqueous material after scrubbing to determine microbial matter reduction using routine microbiology laboratory procedures. The persistence of the effect could also be observed by sampling the area at a specific interval(s) after application.

In the present invention, the primary embodiments are associated with diagnostic microbiology assay reliability (e.g., blood culture and venipuncture cross-contamination), surgical site cleansing, aspirants/irrigates and enteral solutions, and personal protective hygiene measures. Preferred embodiments range from a surface scrub, to rinse solutions, prepackaged douche or enema with dry additives, dry towelette configurations and diuretic enteral solutions. Common lavage diluents include isotonic saline, sterile or bacteriostatic water, antiseptic povidone-iodine solutions, or another suitable irrigating solution. In various embodiments, pre-packaged towelettes would be impregnated with disrupting surface chemistries and a microbiocidal composition, or dry packets of ingredients could be mixed with water for short acting chemical reactions for cleansing, dislodging and flushing of microbial contaminants. Topical scrubbing for personal hygiene as well as ocular cleansing (i.e., eye lids; meibomian glands), nasal and otology rinses, and douches or enemas would also represent the primary embodiments.

Examples and references described in detail herein are directed to various embodiments of the invention. Each is provided by way of explanation and not meant as a limitation of the invention. The features described as part of one embodiment can be used with another to yield still a third embodiment. It is intended that the present invention includes these and other modifications and variations.

In one embodiment of the present invention, a wipe or towelette-like material is impregnated with a fast-drying biocidal nanoparticle formula, preferably halo-fullerenes, and a reactant chemistry admixture, preferably comprised of sodium bicarbonate, acetic acid and a sudsing or foaming agent. The specific amount or concentration of halo-fullerenes used in the composition depend on the intended use. Thus, the composition may comprise from 0.01% to 10% halo-fullerenes. The reactant chemistries, sodium bicarbonate and acetic acid, are ideally added at a range of 1-part sodium bicarbonate to 2-parts acetic acid, to 1-part sodium bicarbonate to 12-parts acetic acid. Alternatively, anhydrous citric acid may be substituted for acetic acid (especially for enteral applications), whereby the ratio of citric acid to sodium bicarbonate ranges from 1-part citric acid to 1-part sodium bicarbonate, to 4-parts citric acid to 1-part sodium bicarbonate. The foaming or sudsing agent of the composition is ideally a non-ionic surfactant at a concentration between 1% and 10% and may comprise common medically appropriate chemistries, including, but not limited to, alkyl polyglucosides, nonylphenols, nonylphenol ethoxylates, polysorbates, and sorbitan esters. Optionally, the use of an anionic surfactant (e.g., sulfate, sulfonate, phosphate, and carboxylates) or amphoteric surfactant (e.g., phospholipids phosphatidylserine, phosphatidylethanolamine, phosphatidylcholine, sphingomyelins, lauryldimethylamine oxide and myristamine oxide) may be substituted or combined with the non-ionic surfactant. The precise concentration of halo-fullerenes, reactant chemistries and non-ionic surfactant to be distributed within this range could be readily determined by one with ordinary skill in the art.

In another embodiment, the dry composition may be layered on the surface of a flexible cleaning wipe such that the halo-fullerenes, reactant chemistries and surfactants are applied as separate and distinct coatings. Layers may be deposited sequentially onto the material and/or separated by a biocompatible, biodegradable, non-toxic and water-soluble matrix, such as polymer film. The overall size and dimensions of the material would be variable, e.g., 2-inch wipes, 4 to 6-inch wipes, or larger configurations as determined by the desired use. The dry composition may also be layered onto a sponge or another coarse material adapted for scrubbing. The material may additionally comprise abrasive particles, fibers or filaments.

Wherein, exposing the antimicrobial wiping material of these embodiments to water would provide topical decontamination. Optionally, the use of anhydrous citric acid may also be substituted for acetic acid, and the use of either nonylphenol ethoxylate or myristamine oxide may be substituted for other non-ionic and anionic surfactants, respectively.

In another embodiment of the present invention, the reactant stimulant and halo-fullerenes may be pre-packaged in a dry packet composition, rehydrated using a suitable aqueous diluent, and formulated for specific applications, e.g., rinsing the mouth or nasal passages. The exclusion of reactive admixtures (e.g., sodium bicarbonate and acetic acid) would also allow for scent and palatability considerations when applied as a nasal or oral rinse solution. It would be obvious to someone skilled in the art that similar adaptations would be compatible for ocular (e.g., meibomian gland cleansing) and otology irrigation, as well. Alternatively, the material would be further compatible as an antimicrobial solution or rinse for food safety applications.

In another aspect of the present embodiment, the dry powder packaged composition could be included or mixed with a common surgical lavage solution to irrigate or aspirate a surgical site, especially in cases when scrubbing the region is not possible. It would be obvious that the composition would be useful as an antiseptic rinse for wounds, burns or other injuries that occur when appropriate medical intervention is not readily accessible (e.g., field dressings, camping, hiking, etc.).

In yet another aspect of the present embodiment, a dry packet composition may be useful as a douche or enema. While the halo-fullerene containing dry packet composition may be comparable to a regimen of antibiotics with respect to vaginal or rectal mucosa, routine topical use for personal hygiene would pose no such risks. Additional product embodiments could include collapsible containers to be used discreetly in various settings.

In the enteral embodiment, an engineered water (hypertonic) powdered drink package directed towards renal and ureter flushing would be combined with botanical diuresis properties to increase fluid excretion and boosted with a dilute hydrophobic halo-fullerene as a urethral biocide. The powdered drink package may comprise 0.01% halo-fullerenes, herbal diuretic(s), and a hypertonic powder containing electrolytes and glucose. Preferably, the diuretic would include one or more botanical diuretic agents such as, but not limited to, *Equisetum arvense* (Horsetail), *Taracacum officinale* (Dandelion root extract), *Apium graveolens* (Celery seed extract), *Crataegus monogyna* (Hawthorne berry), *Juniperus communis* (Juniper berry extract), *Arctium lappa* (Burdock root), *Borago officinalis* (Borage), *Arctostaphylos uva-ursi* (Bearberry leaf extract), *Agothosma betulina* (Buchu leaf extract), *Vaccinium macrocarpon* (Cranberry extract), or *Petroselinum crispum* (Parsley root extract). The hypertonic powder would be calibrated to contain higher solute concentrations than physiologic levels. The carbohydrate solutes may comprise dextrin, monosaccharides (e.g., dextrose, fructose, galactose, etc.), sugar alcohols (e.g., mannitol, sorbitol, erythritol, etc.), polysaccharides (e.g., starch, glycogen, galactogen, etc.), and/or another such sugar solute additive. The electrolyte solutes would be comprised of one or more of the following: sodium, potassium, calcium, magnesium, chloride, hydrogen phosphate, and/or hydrogen carbonate. Optionally, the packet may also comprise a natural or artificial flavoring agent for palatability. A surfactant or emulsifying agent may also be included in the composition.

The following examples are illustrative of the present embodiment invention. Unless otherwise indicated, the percentages herein are based on the weight of the composition.

In an exemplary embodiment, a towelette, wipe, sponge or otherwise flexible material is coated with a dry composition comprising sodium bicarbonate (30%-40%); anhydrous acetic acid (40%-60%); nonylphenol ethoxylate (1%-10%; non-ionic surfactant); and halo-fullerene (0.01%-10%).

In a second exemplary embodiment, a towelette, wipe, sponge or otherwise flexible material is coated with a dry composition comprising sodium bicarbonate (30%-40%); anhydrous acetic acid (40%-60%); myristamine oxide (1%-10%; anionic surfactant); and halo-fullerenes (0.01%-10%). Optionally, anhydrous acetic acid may be substituted for anhydrous citric acid, and myristamine oxide may be substituted for another anionic surfactant.

In a third exemplary embodiment, a towelette, wipe, sponge or otherwise flexible material is coated with a dry composition comprising sodium bicarbonate (30%-40%); anhydrous acetic acid (40%-60%); nonylphenol ethoxylate (1%-10%; non-ionic surfactant); myristamine oxide (1%-10%; anionic surfactant); and halo-fullerenes (0.01%-10%).

In another exemplary embodiment, the dry powder packaged composition comprises sodium chloride (30%-40%); sodium bicarbonate (30%-40%); anhydrous acetic acid (1%-10%); nonylphenol ethoxylate (0.01%-1%; non-ionic surfactant) and halo-fullerenes (0.01%-10%). Wherein, mixing one packet of the dry packaged material with a defined volume of water would result in an isotonic rinsing solution, and inclusion of two packets would provide a hypertonic solution. The packets may be pH balanced and preservative-free. Optionally, the use of anhydrous citric acid may be substituted for acetic acid or removed altogether, and nonylphenol ethoxylate may be substituted for another suitable non-ionic surfactant, or excluded altogether.

In an enteral exemplary embodiment, the powdered drink composition packet would be mixed with water and comprised of halo-fullerene (0.01%-1.0%); 500 milligrams of horsetail (*Equisetum arvense*; diuretic); 20 to 30 grams of a carbohydrate composition; and 6 to 10 grams of an electrolyte composition. Wherein, one powdered drink mix packet would be added to 250 mL of water (or 2 packets to 500 mL of water) and immediately consumed. Optionally, the diuretic composition may include other botanical agents or combinations thereof at specified concentrations. The carbohydrate composition may comprise dextrin, dextrose, fructose, galactose, starch, glycogen, galactogen, mannitol, sorbitol, erythritol, etc., other sugar solute additives, or an admixture of such sugar solute additives. The electrolyte composition is comprised of sodium chloride (10%-20% by weight); potassium chloride (10%-20%); dipotassium phosphate (10%-20%); calcium carbonate (10%-20%); and magnesium carbonate (20%-30%). Optionally, a flavoring agent may be included for palatability.

The embodiments of the invention described herein are exemplary, and numerous modifications, variations and rearrangements can be readily envisioned to achieve substantially equivalent results, all of which are intended to be embraced within the intent and scope of the invention. Alternatively, agricultural and companion animal applications would be obvious to those skilled in veterinary arts, and rinses for home and commercial food processing and safety applications would likewise be obvious to those skilled in food handling, packaging and distribution.

What is claimed:

1. An antimicrobial, antibacterial, antiviral, and antifungal wipe useful for decolonizing, eradicating, and killing pathogenic material, wherein the wipe is coated with a mixture comprising biocidal nanoparticles and a reactant chemistry that is, wherein the mixture of biocidal nanoparticles and reactant chemistry comprises:
   a. Halo-fullerenes,
   b. Sodium Bicarbonate,
   c. Acetic Acid, and
   d. A sudsing or foaming agent
   wherein the reactant chemistry is activated through aqueous immersion
   and
   wherein the halo-fullerene comprises only halogen and carbon atoms.

2. The antimicrobial, antibacterial, antiviral, and antifungal wipe of claim 1, wherein said wipe is a textile or matrix material, and wherein said wipe is a towelette, cloth, sponge or other flexible absorbent material.

3. The antimicrobial, antibacterial, antiviral, and antifungal wipe of claim 1, wherein the fullerenes have a chemical formula of $C_{60}X_6$, $C_{60}X_8$, or $C_{60}X_{24}$, and wherein X is a halogen selected from the group consisting of fluorine, chlorine, bromine, and/or iodine.

4. The antimicrobial, antibacterial, antiviral, and antifungal wipe of claim 1, wherein the concentration of halo-fullerenes is between 0.01% and 10.0% by weight, the concentration of sodium bicarbonate is between 30% and 40% by weight, the concentration of acetic acid is between 40% and 60% by weight, and the concentration of foaming or sudsing agent is between 1.0% and 10.0% by weight.

5. The antimicrobial, antibacterial, antiviral, and antifungal wipe of claim 1, wherein the ratio of sodium bicarbonate and acetic acid is between 1:2 to 1:24.

6. The antimicrobial, antibacterial, antiviral, and antifungal wipe of claim 1, wherein the foaming or sudsing agent comprises one or more non-ionic or anionic surfactants.

7. The antimicrobial, antibacterial, antiviral, and antifungal wipe of claim 1, wherein said wipe is applied to a physiological surface, and wherein said physiological surface consists of skin, optionally including the skin surrounding the genitalia; surgical and needle incision sites; or any region where removal of microbial matter is advantageous.

8. An antimicrobial, antibacterial, antiviral, and antifungal dry powder composition useful for decolonizing, eradicating, and killing pathogenic material, comprising a mixture of biocidal nanoparticles and a reactant chemistry, wherein the mixture of biocidal nanoparticles and reactant chemistry comprises:
   a. Halo-fullerenes,
   b. Sodium chloride,
   c. Sodium bicarbonate,
   d. Anhydrous acetic acid, and
   e. A non-ionic surfactant,
   wherein the reactant chemistry is activated through aqueous immersion
   and
   wherein the halo-fullerene comprises only halogen and carbon atoms.

9. The antimicrobial, antibacterial, antiviral, and antifungal dry powder composition of claim 8, wherein the fullerenes have a chemical formula of $C_{60}X_6$, $C_{60}X_8$, or $C_{60}X_{24}$, and wherein X is a halogen selected from the group consisting of fluorine, chlorine, bromine, and/or iodine.

10. The antimicrobial, antibacterial, antiviral, and antifungal dry powder composition of claim 8, wherein the concentration of halo-fullerenes is between 0.01% and 10.0% by weight, the concentration of sodium bicarbonate is between 30% and 40% by weight, the concentration of acetic acid is between 40% and 60% by weight, and the concentration of foaming or sudsing agent is between 1.0% and 10.0% by weight.

11. The antimicrobial, antibacterial, antiviral, and antifungal dry powder composition of claim 8, wherein addition of water forms an aqueous solution, and wherein said aqueous solution is useful as a wash, rinse, douche, enema, or lavage solution for decolonizing, eradicating, and killing pathogenic material and decontaminating a bodily surface, orifice, cavity, or any other region where removal of microbial matter is advantageous.

12. An antimicrobial, antibacterial, antiviral, and antifungal dry drink powder composition comprising biocidal nanoparticles and a reactant chemistry that is activated through aqueous rehydration, and is useful for decolonizing, eradicating, and/or killing pathogenic material comprising:

a. Halo-fullerenes, b. A botanical diuretic agent, and c. A hypertonic carbohydrate and electrolyte composition, wherein the halo-fullerene comprises only halogen and carbon atoms.

13. The antimicrobial, antibacterial, antiviral, and antifungal dry drink powder composition of claim 12, wherein the halo-fullerenes have the chemical formula of $C_{60}X_6$, $C_{60}X_8$, or $C_{60}X_{24}$, and wherein X is a halogen selected from the group consisting of fluorine, chlorine, bromine, and/or iodine.

14. The antimicrobial, antibacterial, antiviral, and antifungal dry drink powder composition of claim 12, wherein the halo-fullerene concentration is between 0.01% and 1.0% by weight.

15. The antimicrobial, antibacterial, antiviral, and antifungal dry drink powder composition of claim 12, wherein the diuretic agent is *Equisetum arvense, Taracacum officinale, Apium graveolens, Crataegus monogyna, Juniperus communis, Arctium lappa, Borago officinalis, Arctostaphylos uva-ursi, Agothosma betulina, Vaccinium macrocarpon*, or *Petroselinum crispum.*

16. The antimicrobial, antibacterial, antiviral, and antifungal dry drink powder composition of claim 12, wherein the carbohydrate composition comprises one or more of the following: dextrin, monosaccharides, sugar alcohols, and/or polysaccharides.

17. The antimicrobial, antibacterial, antiviral, and antifungal dry drink powder composition of claim 12, wherein the electrolyte composition comprises one or more of the following: sodium, potassium, calcium, magnesium, chloride, hydrogen phosphate, and/or hydrogen carbonate.

18. The antimicrobial, antibacterial, antiviral, and antifungal dry drink powder composition of claim 12 further comprising a natural or artificial flavoring agent.

19. The antimicrobial, antibacterial, antiviral, and antifungal dry drink composition of claim 12, wherein the rehydrated solution is taken enterally and is useful as a hypertonic cellular osmosis and diuresis solution for decolonizing, eradicating, and/or killing pathogenic material and decontamination in vivo.

\* \* \* \* \*